(12) United States Patent
Brisben et al.

(10) Patent No.: US 11,278,232 B2
(45) Date of Patent: Mar. 22, 2022

(54) SIGNAL QUALITY MONITORING FOR MULTIPLE SENSE VECTORS IN CARDIAC DEVICES

(71) Applicant: CARDIAC PACEMAKERS, INC., St. Paul, MN (US)

(72) Inventors: Amy Jean Brisben, St. Paul, MN (US); Venugopal Allavatam, Maple Grove, MN (US); Krzysztof Z. Siejko, Maple Grove, MN (US); Deepa Mahajan, North Oaks, MN (US); Kevin G. Wika, Blaine, MN (US); Keith L. Herrmann, Minneapolis, MN (US); Stephen J. Hahn, Shoreview, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 318 days.

(21) Appl. No.: 16/297,029

(22) Filed: Mar. 8, 2019

(65) Prior Publication Data
US 2019/0216348 A1 Jul. 18, 2019

Related U.S. Application Data

(63) Continuation of application No. 15/297,568, filed on Oct. 19, 2016, now Pat. No. 10,264,989.
(Continued)

(51) Int. Cl.
*A61B 5/341* (2021.01)
*A61B 5/00* (2006.01)
(Continued)

(52) U.S. Cl.
CPC .............. *A61B 5/341* (2021.01); *A61B 5/287* (2021.01); *A61B 5/316* (2021.01); *A61B 5/318* (2021.01);
(Continued)

(58) Field of Classification Search
None
See application file for complete search history.

(56) References Cited

U.S. PATENT DOCUMENTS

| 5,313,953 | A | 5/1994 | Yomtov et al. |
| 5,331,966 | A | 7/1994 | Bennett et al. |

(Continued)

FOREIGN PATENT DOCUMENTS

| EP | 2407097 A1 | 1/2012 |
| WO | 2005011809 A2 | 2/2005 |

OTHER PUBLICATIONS

International Search Report and Written Opinion dated Jan. 19, 207 for International Application No. PCT/US2016/057800.

*Primary Examiner* — Ankit D Tejani
(74) *Attorney, Agent, or Firm* — Seager, Tufte & Wickhem LLP

(57) ABSTRACT

New and alternative approaches to the monitoring of cardiac signal quality for external and/or implantable cardiac devices. In one example, signal quality is monitored continuously or in response to a triggering event or condition and, upon identification of a reduction in signal quality, a device may reconfigure its sensing state. In another example, one or more trends of signal quality are monitored by a device, either continuously or in response to a triggering event or condition, and sensing reconfiguration may be performed in response to identified trends and events. In yet another example, a device may use a looping data capture mode to track sensing data in multiple vectors while primarily relying on less than all sensing vectors to make decisions and, in response to a triggering event or condition, the looped data can be analyzed automatically, without waiting for additional data capture to reconfigure sensing upon identification of the triggering event or condition. In another example a device calculates a composite cardiac
(Continued)

cycle by overlaying signal morphology for a number of cardiac cycles and analyzes the composite cardiac cycle to calculate signal quality metrics.

13 Claims, 15 Drawing Sheets

Related U.S. Application Data

(60) Provisional application No. 62/245,757, filed on Oct. 23, 2015, provisional application No. 62/245,738, filed on Oct. 23, 2015, provisional application No. 62/245,762, filed on Oct. 23, 2015, provisional application No. 62/245,729, filed on Oct. 23, 2015.

(51) Int. Cl.

| | |
|---|---|
| *A61N 1/39* | (2006.01) |
| *A61N 1/05* | (2006.01) |
| *A61B 5/287* | (2021.01) |
| *A61B 5/316* | (2021.01) |
| *A61B 5/318* | (2021.01) |
| *A61B 5/349* | (2021.01) |
| *A61B 5/352* | (2021.01) |
| *A61B 5/364* | (2021.01) |
| *A61N 1/362* | (2006.01) |
| *A61N 1/04* | (2006.01) |
| *A61N 1/365* | (2006.01) |
| *A61N 1/37* | (2006.01) |
| *A61B 5/024* | (2006.01) |
| *A61B 5/0245* | (2006.01) |
| *A61B 5/35* | (2021.01) |
| *A61B 5/283* | (2021.01) |
| *A61B 5/327* | (2021.01) |
| *A61B 5/366* | (2021.01) |

(52) U.S. Cl.
CPC .............. *A61B 5/349* (2021.01); *A61B 5/352* (2021.01); *A61B 5/364* (2021.01); *A61B 5/686* (2013.01); *A61B 5/72* (2013.01); *A61B 5/7203* (2013.01); *A61B 5/7221* (2013.01); *A61N 1/046* (2013.01); *A61N 1/05* (2013.01); *A61N 1/0563* (2013.01); *A61N 1/3622* (2013.01); *A61N 1/3625* (2013.01); *A61N 1/36514* (2013.01); *A61N 1/3704* (2013.01); *A61N 1/3925* (2013.01); *A61N 1/3956* (2013.01); *A61N 1/3987* (2013.01); *A61B 5/0245* (2013.01); *A61B 5/02416* (2013.01); *A61B 5/283* (2021.01); *A61B 5/327* (2021.01); *A61B 5/35* (2021.01); *A61B 5/366* (2021.01); *A61B 5/6869* (2013.01)

(56) References Cited

U.S. PATENT DOCUMENTS

| | | |
|---|---|---|
| 5,709,215 A | 1/1998 | Perttu et al. |
| 6,230,059 B1 | 5/2001 | Duffin |
| 6,393,316 B1 | 5/2002 | Gillberg et al. |
| 6,728,572 B2 | 4/2004 | Hsu et al. |
| 7,248,921 B2 | 7/2007 | Palreddy et al. |
| 7,330,757 B2 | 2/2008 | Ostroff et al. |
| 7,376,458 B2 | 5/2008 | Palreddy et al. |
| 7,392,085 B2 | 6/2008 | Warren et al. |
| 7,496,409 B2 | 2/2009 | Greenhut et al. |
| 7,623,909 B2 | 11/2009 | Sanghera et al. |
| 7,783,340 B2 | 8/2010 | Sanghera et al. |
| 8,160,686 B2 | 4/2012 | Allavatam et al. |
| 8,160,687 B2 | 4/2012 | Warren et al. |
| 8,185,198 B2 | 5/2012 | Palreddy et al. |
| 8,200,341 B2 | 6/2012 | Sanghera et al. |
| 8,457,737 B2 | 6/2013 | Bardy et al. |
| 8,494,630 B2 | 7/2013 | Palreddy et al. |
| 8,565,878 B2 | 10/2013 | Allavatam et al. |
| 8,600,489 B2 | 12/2013 | Warren et al. |
| 8,670,826 B2 | 3/2014 | Warren et al. |
| 8,706,215 B2 | 4/2014 | Kaib et al. |
| 8,712,523 B2 | 4/2014 | Sanghera et al. |
| 8,831,711 B2 | 9/2014 | Freer et al. |
| 8,983,586 B2 | 3/2015 | Zhang |
| 9,119,596 B2 | 9/2015 | Sanghera et al. |
| 9,352,165 B2 | 5/2016 | Zhang |
| 9,451,892 B2 | 9/2016 | Siejko |
| 9,451,893 B2 | 9/2016 | Siejko et al. |
| 9,629,565 B2 | 4/2017 | Siejko |
| 9,924,885 B2 | 3/2018 | Stadler et al. |
| 10,278,601 B2 | 5/2019 | Greenhut et al. |
| 2006/0235476 A1 | 10/2006 | Gunderson et al. |
| 2007/0276445 A1 | 11/2007 | Sanghera et al. |
| 2008/0188901 A1 | 8/2008 | Sanghera et al. |
| 2008/0269813 A1 | 10/2008 | Greenhut et al. |
| 2011/0098775 A1 | 4/2011 | Allavatam et al. |
| 2012/0046563 A1 | 2/2012 | Allavatam et al. |
| 2015/0126883 A1 | 5/2015 | An et al. |
| 2016/0001090 A1* | 1/2016 | Ostroff .................. A61B 5/287 607/5 |

* cited by examiner

SIGNAL QUALITY MONITORING FOR MULTIPLE SENSE VECTORS IN CARDIAC DEVICES

CROSS REFERENCE TO RELATED APPLICATIONS

The present application is a continuation of U.S. patent application Ser. No. 15/297,568, filed Oct. 19, 2016, which claims the benefit of and priority to U.S. Provisional Patent Application Ser. No. 62/245,757, filed Oct. 23, 2015 and titled SIGNAL QUALITY MONITORING FOR MULTIPLE SENSE VECTORS IN CARDIAC DEVICES, U.S. Provisional Patent Application Ser. No. 62/245,738, filed Oct. 23, 2015 and titled MULTI-VECTOR SENSING IN CARDIAC DEVICES WITH SIGNAL COMBINATIONS, U.S. Provisional Patent Application Ser. No. 62/245,762, filed Oct. 23, 2015 and titled MULTI-VECTOR SENSING IN CARDIAC DEVICES WITH DETECTION COMBINATIONS, and U.S. Provisional Patent Application Ser. No. 62/245,729, filed Oct. 23, 2015 and titled MULTI-VECTOR SENSING IN CARDIAC DEVICES USING A HYBRID APPROACH, each filed on Oct. 23, 2015, the disclosures of which are incorporated herein by reference.

BACKGROUND

A number of cardiac rhythm management products are available for the use in diagnosis and treatment of various conditions. These may include, for example, subcutaneous, transvenous, or intracardiac therapy devices such as pacemakers, defibrillators and resynchronization devices. Implantable, external and/or wearable cardiac monitors are also available. External or wearable therapy products may include defibrillator vests and external pacemakers, as well as automatic external defibrillators.

In some cardiac rhythm management products, a plurality of sensing electrodes may be provided for use in obtaining cardiac electrical signals for analysis of the patient's cardiac status. Some such products have sufficient sensing electrodes to define more than one sensing vector, with each sensing vector defined by a combination of 2 or more electrodes. With multiple sensing vectors available, some systems may take steps to select a primary sensing vector, as not all sensing vectors may be equally suitable at a given time for a given patient to accurately assess cardiac status. As the patient engages in daily activity, such as exercise or merely changing postures, and comes into proximity with external sources of electromagnetic interference, different vectors may perform differently. If the patient's cardiac state changes by, for example, going from a normal sinus rhythm to experiencing a rate induced bundle branch block, an atrial arrhythmia, or due to other pathologies, and/or changes in medication, different sensing vectors may again provide different signal quality.

New and alternative approaches to the monitoring of cardiac signal quality across one or more sensing vectors are desirable.

OVERVIEW

The present inventors have recognized, among other things, that a problem to be solved is the need for new and alternative approaches to the monitoring of cardiac signal quality for external and/or implantable cardiac devices. In one example, signal quality is monitored continuously or in response to a triggering event or condition and, upon identification of a reduction in signal quality, a device may reconfigure its sensing state. In another example, one or more trends of signal quality are monitored by a device, either continuously or in response to a triggering event or condition, and sensing reconfiguration may be performed in response to identified trends and events. In yet another example, a device may use a looping data capture mode to track sensing data in multiple vectors while primarily relying on less than all sensing vectors to make decisions and, in response to a triggering event or condition, the looped data can be analyzed automatically, without waiting for additional data capture to reconfigure sensing upon identification of the triggering event or condition. In another example a device calculates a composite cardiac cycle by overlaying signal morphology for a number of cardiac cycles and analyzes the composite cardiac cycle to calculate signal quality metrics.

This overview is intended to provide a summary of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
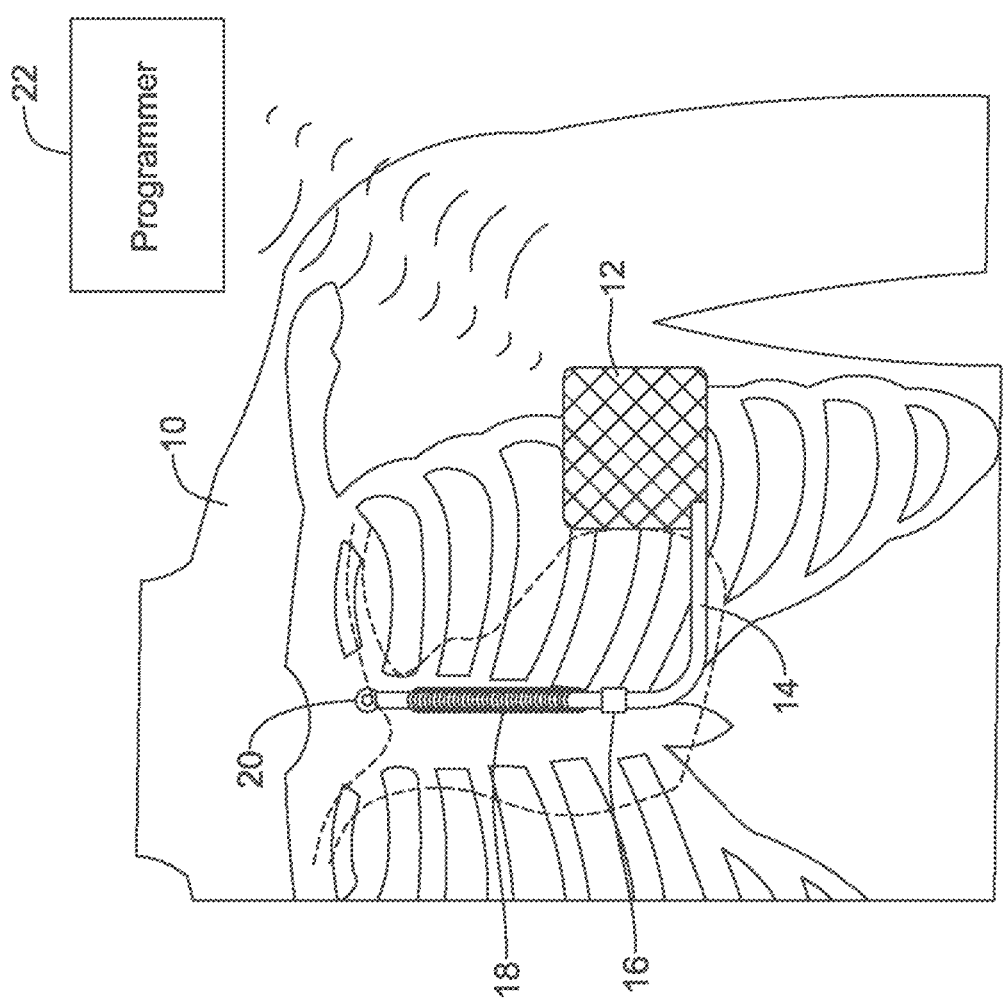
FIG. 1 shows an illustrative implantable medical device system with multiple sensing vectors available.

FIG. 1 shows the S-ICD System™ from Cameron Health, Inc., and Boston Scientific Corporation as implanted in a patient. The system is implanted in a patient 10 with a canister 12 in the left axilla at about the level of the cardiac apex. A lead 14 is placed subcutaneously, beneath the skin and over the ribcage of the patient, with a first portion extending along the inframammary crease to the xiphoid, and then superiorly parallel to and about 1-2 cm to the left of the sternum. A proximal sense electrode 16, shocking coil electrode 18, and distal tip sense electrode 20 are provided along the parasternal portion of the lead 14. The entire system is implanted outside of the ribcage.

The canister 12 may further include such components as would be appropriate for communication (such as RF communication, inductive telemetry or other suitable communication linkage) with an external device such as a programmer 22, or remote monitoring device. For example, during an implantation procedure, once the canister 12 and lead 14 are placed, the programmer 22 may be used to activate the canister 12 and/or direct/observe diagnostic or operational tests. After implantation, the programmer 22 (or remote monitoring device, such as a bedside monitor) may be used to non-invasively determine the status and history of the implanted device. The programmer 22 in combination with the canister 12 may also allow reporting of statistics, errors, history and potential problems to the user/medical practitioner, and may also allow for updating of programming in the canister 12.

There are several individual and combinational sensing vectors available with this implantation. In the commercial implementation there are three available sensing vectors: between electrode 16 and electrode 20, between electrode 16 and the metal housing of the canister 12, and between electrode 20 and the metal housing of the canister 12. If desired, the system could also be modified to use electrode 18 as a sensing electrode, paired with any of electrodes 16 and 20 or the metal housing of the canister 12. Moreover, it would be possible to combine two electrodes as a single pole for sensing, if desired.

The illustration in FIG. 1 is just one example. In additional examples, an implantable or wearable cardiac monitor may have multiple electrodes on a housing and/or lead to define two or more sensing vectors. Leadless devices, such as leadless cardiac pacemakers for implantation inside the heart, may have multiple sensing electrodes on or extending from a canister or housing to define multiple sensing vectors. Wearable defibrillators or pacemakers may also provide multiple cutaneous electrodes on the anterior and/or posterior thorax of the patient, and may even include indifferent electrodes elsewhere such as on a limb. Transvenous and/or epicardial implantable devices may have an active housing adapted for use in sensing along with plural electrodes for sensing on one or more leads, as is well known in the art. For example, a transvenous device may have a right ventricular lead with atrial and ventricular sensing electrodes as well as an indifferent electrode on the canister. Additional sensing data may be mathematically derived from combinations of the physical vectors provided by the sensing electrodes, including, for example derivation of traditional sense vectors from a 12-lead ECG.

For any of these systems, the availability of multiple sensing vectors poses several questions, including how to determine which of several sensing vectors is or is not performing well, and how to decide whether to switch from one sensing configuration to another. The first generation of the S-ICD System shown in FIG. 1 incorporated sensing vector selection methods in the clinical setting while in communication with a programmer. Some details of such methods are discussed in U.S. Pat. Nos. 7,392,085, 7,623, 909, and 8,200,341, the disclosures of which are incorporated herein by reference. The device did not automatically switch sensing vectors in response to identified sensing signal quality metric changes.

Some additional background discussion of the use of multiple vectors and sensing therewith is shown in U.S. Pat. No. 5,313,953, as well as U.S. Pat. No. 5,331,966 which additionally shows a device with multiple housing electrodes for sensing. While these prior discussions identify the possibility of ambulatory vector quality monitoring and switching, and/or combining multiple sense vector signals together, there remains additional need for alternatives and new devices and methods to perform signal quality monitoring, sense vector switching, and/or to provide for combining multiple sense vectors together.

Figure 2:
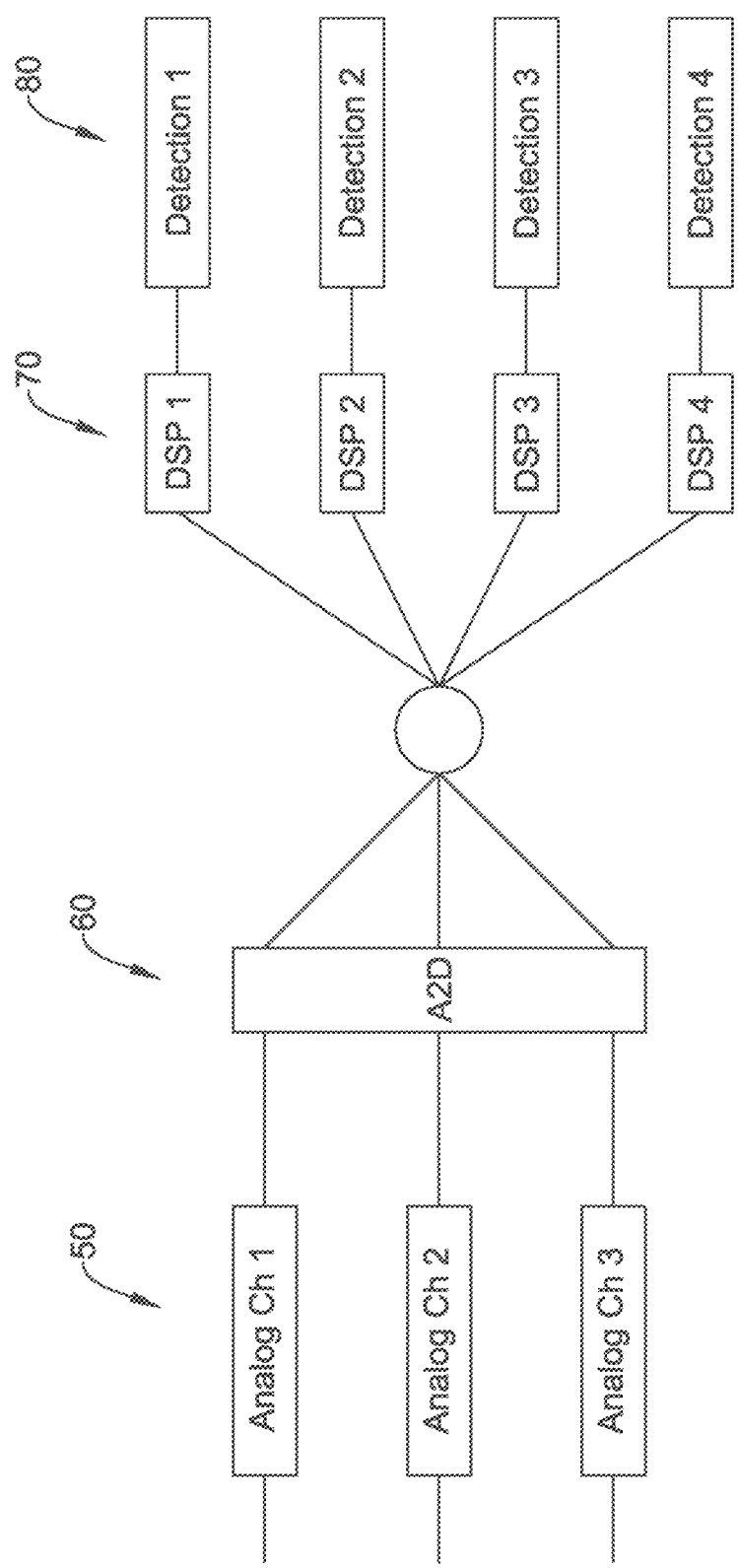
FIG. 2 shows schematically an illustrative input circuit design.

FIG. 2 shows an illustrative sensing input system. A plurality of analog input channels are defined as indicated at 50. The analog channels 50 may be dedicated or hard wired to a particular combination of sensing electrodes, or may be defined using a multiplexor or other switch array to couple to pairs or groups of sensing electrodes such as described above and/or in association with FIG. 1. The individual channels may include DC blocking, bandpass, notch, bandstop, 50/60 Hz blocking, and/or other filtering circuitry as well as amplification circuitry such as a low noise amplifier, either as stand-alone circuits or operating cooperatively with an analog to digital conversion (ADC) circuitry 60. Any suitable ADC circuitry may be used, including a wide array of such devices known in the art including delta-sigma, successive approximation, Wilkinson, ramp-compare, delta encoded, pipeline, integrating, etc.

In some examples only a subset of the analog channels 50 are converted at any given time; in other examples all of the analog channels 50 may be converted. The plurality of digital signals output by the ADC circuit can be assessed on one or plural digital signal processors (DSP) 70, or may be analyzed together in single processor. For power saving purposes, and to take advantage of modular design, it may be suitable to use dedicated DSP to yield a digital signal for use in detection circuits 80. Any suitable DSP circuit can be used at 70. One element of DSP may be the inclusion of a digital filtering circuit to narrow the band of signals to a range generally between about 10 and 40 Hz, though wider or narrower ranges may be used. In addition, line signal filtering at 50 or 60 Hz, depending on geography, may be implemented in the DSP.

In some examples the individual detection blocks at 80 each use a separate cardiac cycle detection method to identify heart beats for use in one or more of defining a cardiac cycle signal for morphology (shape) analysis, and or to count cardiac cycles per unit time to generate a cardiac rate for a given chamber of the heart. Individual detection blocks at 80 may each use the same method of cardiac cycle analysis, or different methods may be selected for different digital signals. For example, if one detection line is configured for use on a signal captured using two intracardiac electrodes, and a different detection line uses signal captured using two subcutaneous electrodes, the detection lines would likely each use a different mode of detection, as the intracardiac signal will look quite different from the subcutaneous signal. Some examples of cardiac cycle detection (also sometimes referred to as R-wave or beat detection) are shown in U.S. Pat. Nos. 8,565,878 and 5,709,215, the disclosures of which are incorporated herein by reference. Several methods are known in which a time varying threshold compared against the received cardiac signal until the threshold is crossed, at which point a beat or new cardiac cycle may be declared.

At various places in the diagram of FIG. 2 there are possible opportunities to observe signal quality. For example, an understanding of signal quality can be generated for each of the individual signals by observing the duration of time spent away from baseline in a given sensing vector, where the assumption is that the various filtering which is applied will cause a good signal to be at or near baseline most of the time except during excursions caused by the cardiac signal. However, in several embodiments, additional signal quality metrics are generated in reliance on the outcomes of the detection blocks 80. For example:

When a cardiac cycle is detected, most detection schemes are directed toward identifying a particular one of the several components of a typical cardiac cycle (the P, Q, R, S or T waves, for example, or the QRS complex). The detected cycle can then be divided into two windows: the desirable signal (i.e. the R-wave or QRS complex for most ventricular driven cycle methods, or a P-wave for an atrial cycle detector), and the undesirable signal (the T-wave or P-wave or, simply, anything that is not the desirable signal). By comparing the peak or average amplitude in the desirable signal window to the that of the undesirable signal window or to the average of the entire signal (such as a root-mean-square), the signal to noise ratio (SNR) or its inverse, the noise to signal ratio, may be calculated. A high SNR, in some examples, indicates a good quality signal, while a low SNR indicates a poor quality signal.

In similar fashion, the desirable signal may be measured to generate an average or peak amplitude of the desirable signal itself. A high amplitude signal, (within bounds that avoid saturation of input circuitry) may be considered indicative of a good quality signal, while small amplitudes may indicate poor quality signals.

Cardiac cycle detection allows identification of beat rate, which can be validated by use of alternate methods of beat rate calculation such as by reference to a second or more calculation, such as heart sounds, pulse oximetry, blood pressure monitoring, use of a second device, or by comparison of the rate as calculated in one sensing vector to rates in other vectors, or by the comparison of the rate as calculated using cardiac cycle or beat detection to an autocorrelation such as that of U.S. patent application Ser. Nos. 14/819,817, 14/819,851, and 14/819,889, the disclosures of which are incorporated herein by reference. If the rate as calculated in a particular sensing vector is found to be incorrect, some examples may conclude that the signal quality of that particular sensing vector is poor.

Cardiac cycle detection may undergo beat validation to ensure the absence of noise, such as by counting turning points in the cardiac signal either at the time of the detection of a new cardiac cycle or between detections of cardiac cycles, or by other noise detection methods. The signal may also be analyzed for saturation or wandering of the signal from baseline such as described in U.S. Pat. Nos. 7,248,921, 8,712,523, and 8,831,711, the disclosures of which are incorporated herein by reference. If noise, saturation or baseline wander are detected, some examples may conclude that the signal quality of that particular sensing vector is poor.

Detected cardiac cycles may be analyzed for overdetection. Some examples may be found in U.S. Pat. Nos. 8,160,686 and 8,160,687, the disclosures of which are incorporated herein by reference. If overdetection is found, some examples may conclude that the signal quality of that particular sensing vector is poor.

In addition to the above cardiac-cycle triggered analyses, asynchronous signal analysis may be performed on blocks of data (for example, 1 to 10 seconds of data, or more or less) to determine baseline stability, spectral content, or the existence of significant external noise.

Temporal variability of cardiac cycle detection time relative to peak times (or other reference point), for example, the period between a detection threshold crossing to the R-wave peak, may also be used as a signal quality metric.

Variability of the R-wave, QRS amplitude, energy contained in the QRS complex, or other feature peak or average amplitude or magnitude, or energy content, may also be used as a signal quality metric.

Each of these examples may be used as a signal quality metric. Signal quality metrics may be used as a trigger to perform further analysis, as a measure of signal quality, or as an input to a data trend of signal quality.

For example, a rate validation trend may determine how closely a cardiac cycle or beat based rate analysis matches a validation analysis from another vector, source or method; absolute mismatch or a trend away from matching may be observed. In other examples, the frequency with which a poor signal quality marker (such as low SNR or amplitude, or identified noise, saturation, baseline wander, or overdetection) occurs may be tracked; increasing frequency would indicate a loss of signal quality.

Figure 5:
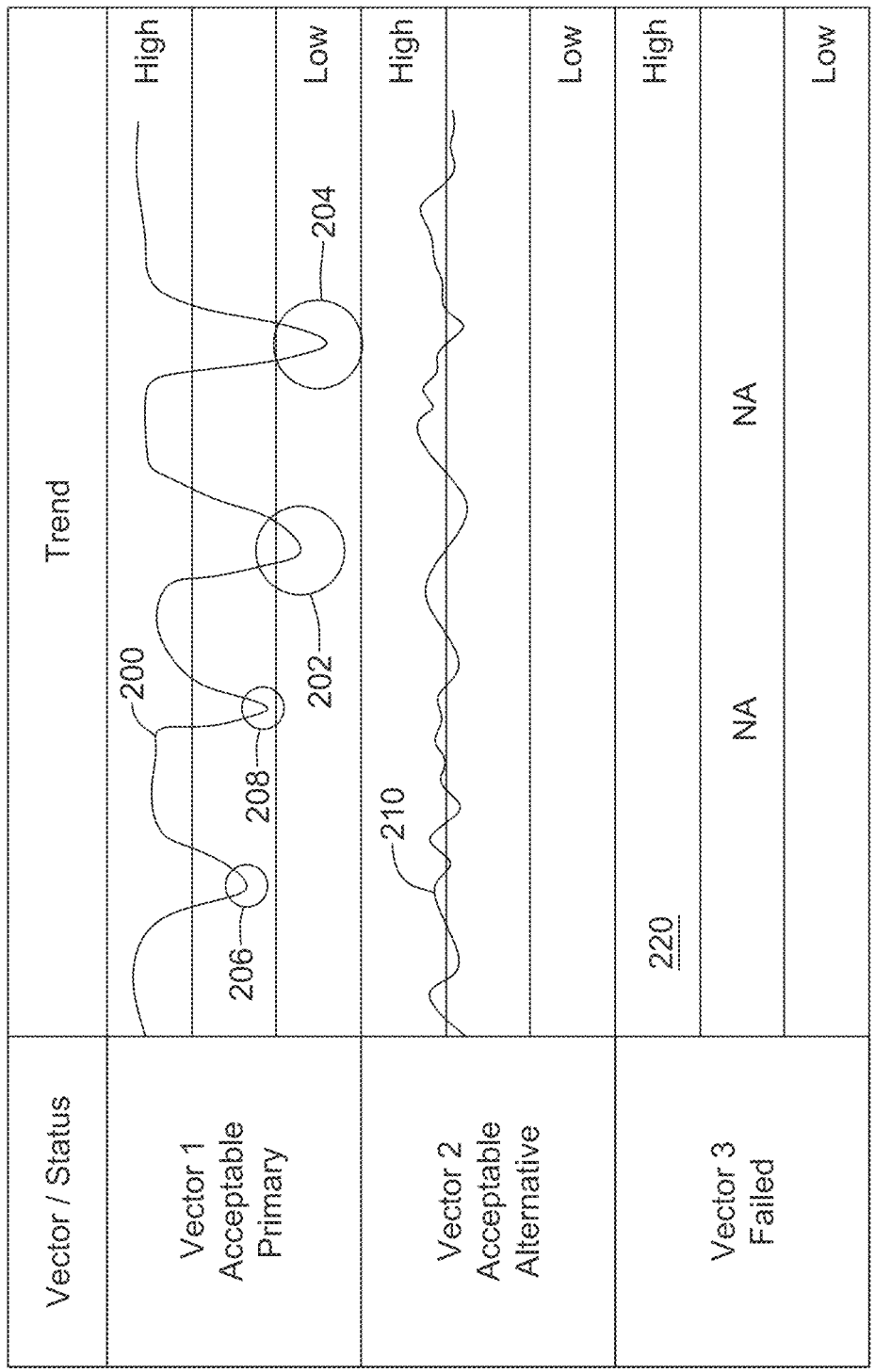
FIG. 5 illustrates trending of sensing vectors.

For example, it has been noted in some instances of use of a system as in FIG. 1 that the signal quality, in terms of amplitude and signal to noise ratio, when measured in clinic, may not remain consistent over time. Consider a hypothetical patient in whom a sensing vector analysis is performed at a first clinical follow-up. For the hypothetical patient, a best performing sensing vector is identified as a sensing vector using electrode 20 and the canister 12 of a system as in FIG. 1. For many patients, the use of a single snapshot in time of the signal quality will provide acceptable performance for the life of the device. However, for this hypothetical patient, at a subsequent clinical follow up, the patient's device indicates one or more recorded episodes of inappropriate therapy or inappropriate arrhythmia identification without therapy (an "untreated episode"), with very low signal amplitude in the recorded episode. At the subsequent follow-up, the default sensing vector, however, shows very good signal quality, just like it did at the first follow-up. In the hypothetical patient, the physician may change the sensing vector in light of the recorded episodes to use a different sensing vector (for example, electrode 16 and the canister 12) showing at least adequate signal quality, even if that different sensing vector does not have the best signal quality at the follow-up. In several real world cases, this approach has been observed to resolve the poor ambulatory sensing, without necessarily providing a complete understanding of why, as the physiological root cause can be elusive. A device configured to use trending of signal quality data, for example as shown by FIGS. 3 and 5 below, can select a vector having more consistent performance without requiring physician intervention.

In some examples, rather than being used as signal quality metrics, one or more of the above listed items may be used as a trigger for performing a signal quality analysis. In an illustration, repeated identification of noise or overdetection may be used as a trigger to perform an overall signal quality analysis in which sensing may be reconfigured.

Figure 3:
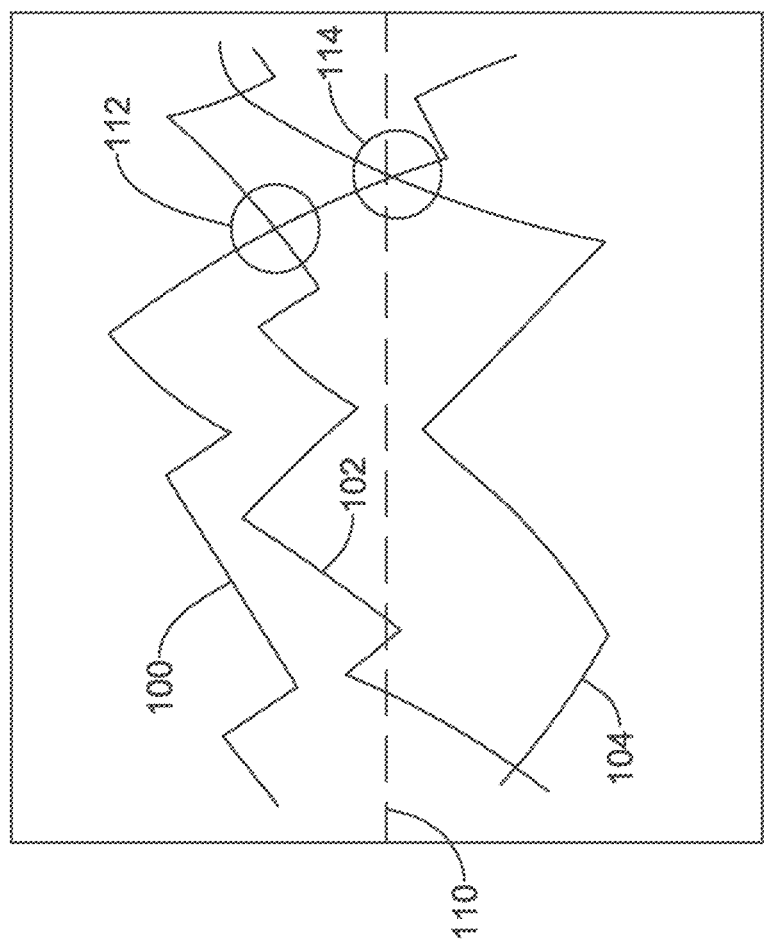
FIG. 3 illustratively shows sensing quality of sensing vectors changing with time.

FIG. 3 illustratively shows sensing quality of sensing vectors changing with time. The vertical axis of the figure represents a signal quality metric, which may be any of the above, configured such that the upper portion of the figure is "good" or "better", while the lower portion of the figure is "poor" or "worse". The horizontal axis represents time.

The signal quality metric for a first sensing vector is represented at 100, for a second sensing vector at 102, and for a third sensing vector at 104. Initially, the first vector 100 scores best of the three and may be selected as a primary sensing vector, to the exclusion of the other two 102, 104. In an alternative example, each vector 100, 102, 104 is used in a combination analysis that applies different weights to data for each vector 100, 102, 104, in which the vector 100 having a highest quality would be most heavily weighted, while a vector 102 (at least initially) having the lowest quality would be least heavily weighted.

As time passes, for example throughout a day, or during a period of exercise or movement, or simply due to the sometimes random nature of cardiac signal quality over time, the vectors 100, 102, 104 perform differently. A threshold is provided at 110. In several illustrative examples, threshold 110 is an alert threshold indicating that a currently selected sensing configuration or vector may not be providing desirable performance, and may be used as a trigger to engage in analysis of the sensing configuration and/or selection of a new sensing configuration. In an alternative example, threshold 110 may instead serve as an acceptability threshold above which a vector is considered to perform well enough to be useful, and below which a vector is considered to perform too poorly to be relied upon. The threshold 110 may, in an alternative example, be a threshold above which a vector is deemed good enough to be used standing alone, and below which the vector would be combined with some other vector to yield acceptable performance.

As shown at 112, eventually the quality metric for the second vector 102 surpasses that of the first vector 100. Still later, the first vector 100 drops below not only the third vector 104, but also the threshold 110, as shown at 114. In this example, over time, the reliance on first vector 100 becomes misplaced. However, the sensing vectors 100, 102, 104 may behave unpredictably, making it necessary to consider carefully when to switch vectors and which to use.

In addition, it should be noted that a normal sinus rhythm, with a large QRS complex and relatively small P and T waves, and with several hundred milliseconds of time passing between QRS complexes, is often relatively easy to sense and will score highly in many metric measures such as a signal to noise ratio, or a probability density function determining whether the signal is at or near baseline most of the time. On the other hand, a polymorphic tachyarrhythmia or ventricular fibrillation will score poorly on these same metrics, even if the sensing is perfect. Such signals are unpredictable in nature and detections may appear to generate overdetection or noise, or low SNR and amplitude, for example, even when the detected signal is being handled correctly. As a result it is also desirable to ensure a metric showing poor signal quality is truly a reflection of poor sensing and not the result of an arrhythmia.

Figure 4:
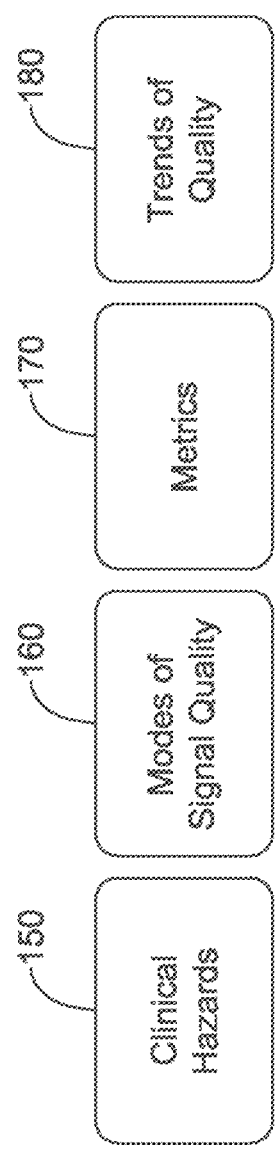
FIG. 4 shows in block form several inputs to a sensing quality monitor.

FIG. 4 shows in block form several inputs to a sensing quality monitor. An understanding of relevant clinical hazards or risks 150 is helpful. Illustrative clinical hazards or risks may include outcomes at the algorithm or device output level, often visible or apparent to one or more of the physician and/or patient. Examples include inappropriate therapy, oversensing, discrimination errors, long time to therapy, and undersensing. When any of these occurs a corrective action may be undertaken.

Modes of signal quality 160 are qualitative descriptions, provided as one or more "root causes" that result in the described clinical hazards 150 during expert event analysis after the events take place. Some examples include elevated T-waves, low signal amplitudes, failure of a stored template ostensibly recorded to match normal sinus rhythm to continue to accurately reflect a normally conducted beat, presence of noise, random variability of detection, unusually wide cardiac signals, and various other factors can come into play. For example, oversensing as a clinical hazard may have a root cause of T-wave oversensing, or a low signal amplitude which causes detection profile usage to fail, or failure of a template match to allow accurate assessment of whether true cardiac beats are being detected.

Specific metrics 170 provide quantitative measurements to the qualitative modes of signal quality 160 and may include, for example, measured ratio of the R-wave to T-wave amplitude, measures of the R-wave amplitude, correlation scores for detected beats to a stored template or between detected beats, counts of zero crossings, turning points or inflection points in a signal (indicative of non-cardiac noise, often), variation of the detected signal from one beat to another (amplitude and width, for example), spectral information (such as a fast Fourier transform or wavelet analysis of captured signal blocks), detected patient motion or posture, and/or sense vector impedance.

From these inputs, including in particular the metrics 170 that quantify the modes of signal quality 160, sensing vector quality trends 180 are tracked in some illustrative examples. To summarize the overall approach for some examples, the clinical hazards 150 indicate, at high level, what happened, the mode of signal quality 160 indicates why something happened, the metrics 170 quantify what happened (the mode), and the trends 180 allow for long term tracking of one or more metrics 170 for one or more sensing vectors.

FIG. 5 illustrates trending of sensing vectors. The example incorporates several concepts, some of which may be used standing alone or in different combinations. A trend is shown at 200 for Vector 1, and is compared against High and Low thresholds as shown. As indicated at the left, Vector 1 in this example has been initially selected as a primary sensing vector or default sensing vector. A trend 210 is shown for another vector, Vector 2, which as indicated at the left is also considered an acceptable vector but which, at least initially, is identified as an alternative to Vector 1 in the event that Vector 1 deteriorates.

Following the trend over time, Vector 2 remains at around the high quality threshold, but does not often exceed the High threshold. Vector 1, on the other hand, is well above the High threshold as shown at 200, but begins to show dips in quality over time. At 202, the quality dips below the Low threshold. This may serve as a triggering event for reassessing the Primary and Alternative vector designations. A short time later, as shown at 204, Vector 1 again drops below the Low threshold. The repeated crossing of the Low threshold may serve as a separate trigger for reassessment of the Primary and Alternative vector designations.

At 206 and 208, the quality of Vector 1 dips into the "ok" region between the High threshold and Low threshold. At these times, the quality of Vector 2 remains greater than the quality of Vector 1. This, or any time that the quality of the Alternative vector is greater than the quality of the Primary vector, may serve as a triggering event for reassessing the Primary and Alternative vector designations.

Also in FIG. 5, a third vector, Vector 3, is indicated as being available. However, Vector 3 is shown as having failed during a prescreening process, thus no trend is shown as indicated at 220. Such a vector may fail during an initial screening process in which, for example, the patient is asked to assume a variety of postures. Failure of a vector may be flagged if the vector fails to perform in one or more postures by having a very low amplitude or poor signal to noise ratio, for example. In one example, a vector may fail because it has highly variable performance in different patient postures, such that changes in signal quality for that vector happen so quickly that the device may not be able to react to change sensing vectors without creating a clinical hazard. In one illustration, a physician may mark a sensing vector as failed, thereby disabling use of that sensing vector, in response to an episode of inappropriate therapy or a long time to therapy occurring. Vector "failure" status may be omitted.

In another example, reconfiguration may be performed after the second Low threshold crossing 204 of Vector 1 as follows: the number of Low threshold crossings for Vector 1 may be counted during a relevant time period (one minute, one hour, or even up to one day or longer, for example). Repeated Low threshold crossings may cause Vector 1 to be deemed unacceptable, even if the vector shows a High signal quality at the time of reassessment for reconfiguration purposes. This is because the variability of the signal quality vector is large, and it may be that in the particular method, the somewhat lower scoring, on average, of Vector 2 is preferred because it is consistent over time, rather than showing large variability. Further details for a number of specific examples are shown below.

Figure 6:
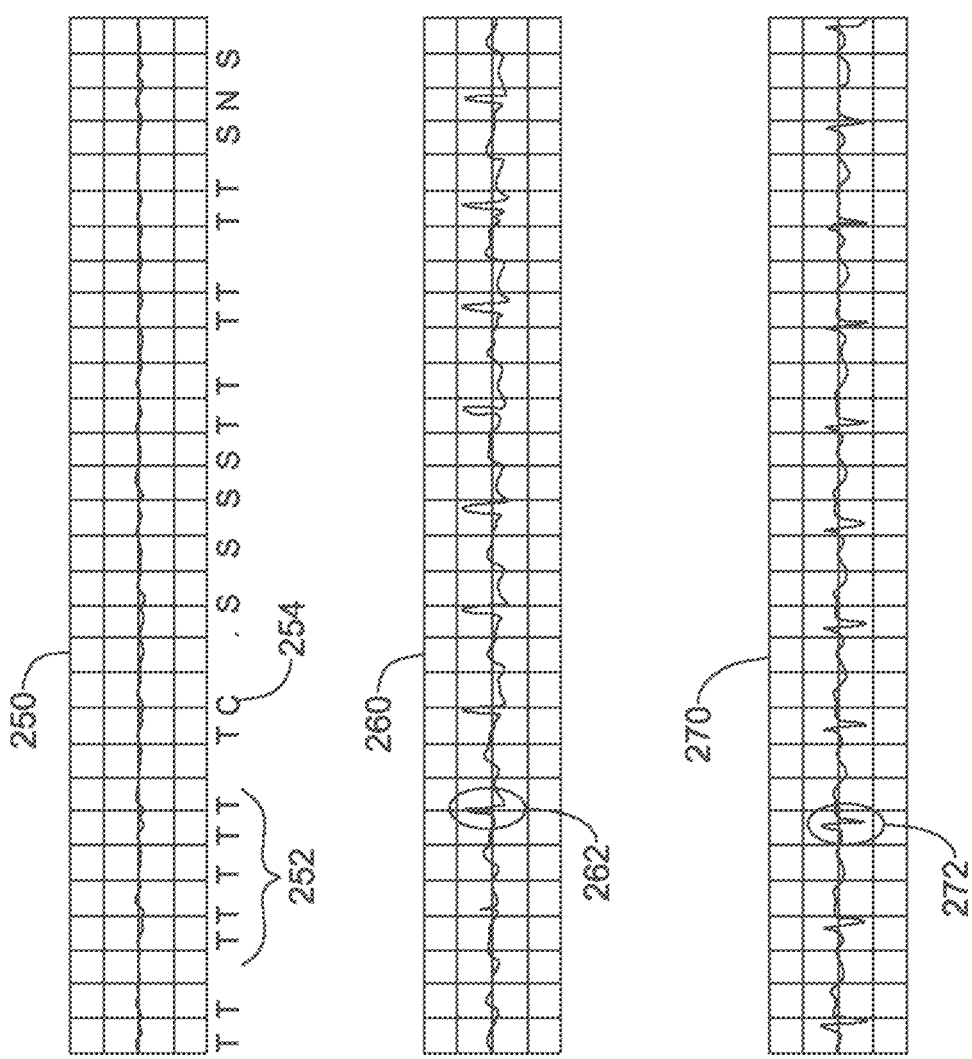
FIG. 6 shows a hypothetical episode of inappropriate arrhythmia identification across multiple vectors.

FIG. 6 shows a hypothetical episode of inappropriate arrhythmia identification across multiple vectors. In this example, a primary sensing vector has previously chosen, and the sensed cardiac signal is shown at 250, with detection markers shown below the signal 250 where "T" indicates a treatable tachyarrhythmic beat, per applied discrimination criteria. After a run of "T" markings 252, a charge begin marker is shown at 254, indicating that the device has determined, based on analysis of the signal 250, that a treatable arrhythmia is occurring. However, to the skilled artisan, it would be apparent that signal 250 is simply a very small signal that does not appear to actually demonstrate an arrhythmia.

In the hypothetical of FIG. 6, the cardiac signals for second and third vectors are shown at 260 and 270. However, in this example, the presumption is that only the primary or default vector signal 250 is being actively analyzed. It can be seen in the second vector 260 that a fairly normal non-arrhythmic signal is occurring with reasonable amplitude beats 262, at a rate shown illustratively as about 100 beats per minute. Likewise the third vector 270 is showing reasonable beats 272.

Figure 7:
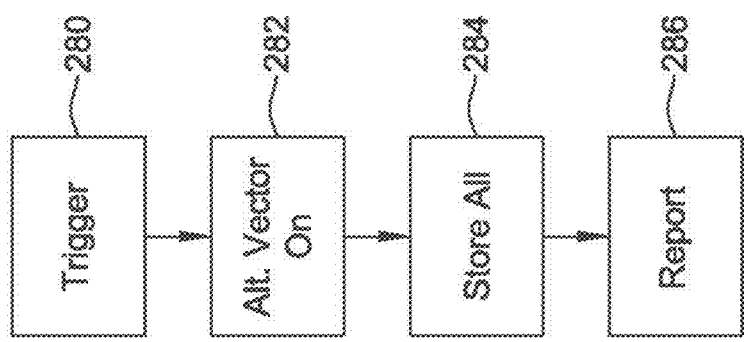
FIG. 7 is a block flow diagram for an illustrative method.

A situation as shown in FIG. 6 gives rise to a method illustrated in FIG. 7. Upon identifying a trigger 280, one or more alternative vectors is enabled as shown at 282. During and/or following the trigger 280, data from each activated vector is stored as shown at 284. The data from multiple recorded vectors are presented together to the treating physician or to some other performance monitor.

The trigger 280 may take several forms, some of which are described above. For example, identification of an elevated rate condition may be a trigger. In another example, identification of a plurality of fast or tachyarrhythmic cardiac cycles may be a trigger. In some examples, an X/Y analysis or number of intervals to detect (NID) analysis may be used to determine whether to declare a treatable episode; for some such examples, the trigger 280 may be same as or a lower boundary than the threshold to declare a treatable episode. In other examples, rather than being related to potentially treatable condition, the trigger 280 may be more of a diagnostic trigger such as the identification of one or more of a long pause between detected cardiac cycles, identification of noise, identification of frequent overdetected cardiac cycles, or failure to consistently match a template, for example. The trigger 280 may also be a high variability in the amplitude of peak values (or some other fiducial point) or high temporal variability in detection times relative to peak amplitude timing, or other fiducial point within the cardiac cycle or signal.

In this example, the approach taken is to preserve a primary sensing vector through an episode but also to capture additional sensing vector data for later troubleshooting purposes. A report 286 may include simply showing the various signals from alternate vectors in some examples. In other examples, a report 286 may provide a simulation of how the alternate vectors would have been analyzed using a device's programmed settings (such as the rate boundaries for defining treatable or enhanced analysis zones).

In an illustrative example, a device may be configured to trigger a sensing vector quality assessment after an episode of tachyarrhythmia is declared. A sensing configuration may be preserved until the tachyarrhythmia episode is over. However, once the episode ends, review of the data captured with each of the existing configuration and one or more alternative configurations or sensing vectors can be reviewed in part to determine whether the tachyarrhythmia episode was correctly declared and/or treated (if therapy was provided). The sense vector configuration may also be reassessed using the data captured during the tachyarrhythmia episode, particularly if the episode was incorrectly declared.

In another example, if therapy is delivered to a patient and a detected arrhythmia is successfully converted, captured sense data from several vectors may be reviewed after the successful conversion. The purpose here may be to determine whether there are any sensing configurations that would have failed to identify the converted arrhythmia and, if so, to mark those configurations as failed or at least store a suggestion that those configurations be treated as failed, to avoid later reconfiguration to a poorly performing sensing vector. Alternatively, the data for an episode may be reviewed to determine whether use of a different sensing vector would have allowed therapy to be delivered to the patient more quickly, to reduce the potential hazard to the patient of syncope in the case of ventricular fibrillation, for example.

Figure 8:
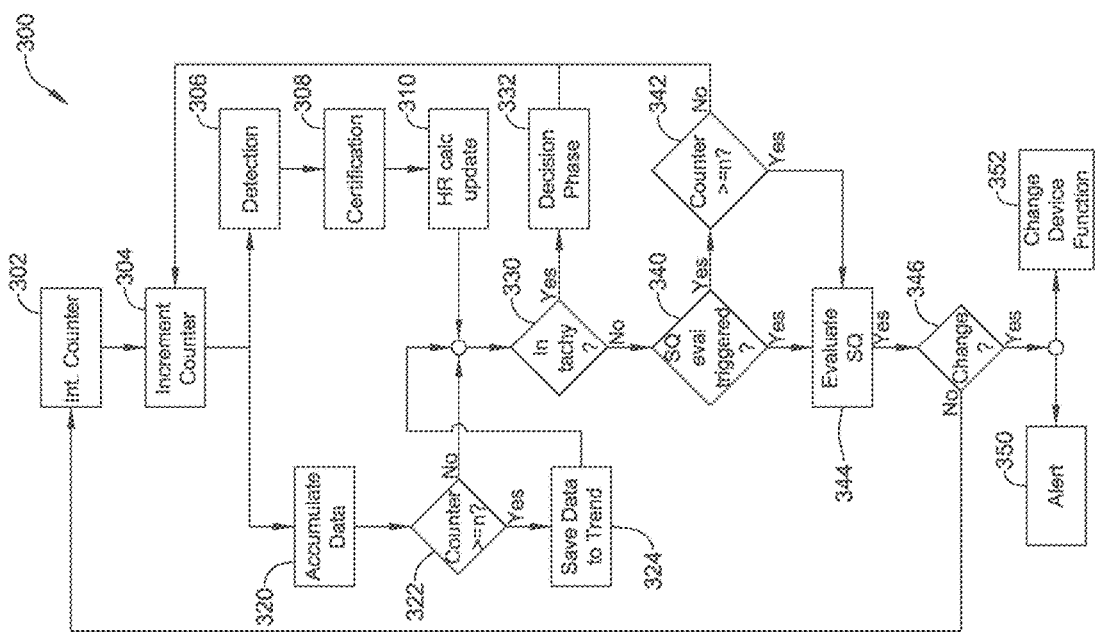
FIG. 8 is a block flow diagram for another illustrative method.

FIG. 8 is a block flow diagram for another illustrative method. The illustrative method 300 provides for ongoing, occasional, or periodic assessment of data trends for sensing vectors. In the illustrative method, a counter used to track the state of the assessment is initialized at 302, and then incremented at 304. A signal analysis track is shown at 306/308/310 as including event detection 306, certification of the event at 308 (which may include the identification and elimination of noise or overdetection, for example), and calculation of the heart rate 310.

In parallel with the signal analysis track 306/308/310 is a sensing vector analysis track at 320, 322, 324. At 320 the sensing vector analysis includes accumulating data on one or several sensing vectors. The data may be analyzed as it is gathered and accumulated or analysis may take place in response to a triggering condition. The data that is accumulated can be summarized and trends calculated therefrom periodically (for example, after a set period of time or quantity of detected cardiac cycles—blocks 322/342) or occasionally (for example in response to a trigger—block 340). In the illustration, a decision block at 322 determines whether the counter has incremented enough to exceed a threshold ("n") and, if so, the accumulated data may be stored away or saved to a trend as shown at 324.

The signal analysis track 306/308/310 and sensing vector analysis tracks 320/322/324 merge again at decision block 330. The decision block at 330 determines whether the existing sensing configuration has determined that a tachy (tachyarrhythmic or high rate) condition exists. If so, a decision phase is entered at 332, and the analysis returns to 304. Thus, in the example shown, the existence of a tachy condition at 330 bypasses further analysis of the sensing vector quality in order to avoid inappropriate under-sensing during a treatable arrhythmia. In other examples, such a bypass may be omitted, and instead of returning to block 304 after the decision phase 332, the analysis can pass to 340 from either of 330 or 332.

At 340, the method determines whether a signal quality sensing evaluation has been triggered by reference to a triggering event or condition. If so, the signal quality analysis takes place at 344. If no triggering event has taken place, the method determines at block 342 whether periodic evaluation is to be performed by determining whether the counter has exceeded a threshold. If neither occasional (340) nor periodic (342) signal quality analysis is called, the method returns to block 304.

The evaluation of signal quality 344 may occur according to any of the embodiments shown above and/or below for such evaluation. For example, trends and other data may be analyzed. In particular, one or more of the signal metrics calculated over the n detections can be compared across the sense vectors, compared to a threshold, or compared to an historical trend. The evaluation of signal quality 344 may take the form of determining whether a current configuration is, and has been historically, performing adequately and, if so, leaving the current configuration in place or, if not, assessing whether a better configuration is available. The evaluation of signal quality 344 may instead take the form of determining whether a current configuration is performing inadequately and, if so, selecting a "best" different sensing configuration or, if not, leaving the current configuration in place. In still another approach, the evaluation of signal quality 344 may be a de novo review of all available sensing configurations to select a best available.

If the evaluation of sensing quality 344 determines that no change is needed, as noted at block 346, the method returns to block 302 and re-initializes the counter. If a configuration change is found to be necessary or advisable, block 346 may enable one or both of blocks 350 and 352. At block 350, an alert may be set or issued by, for example, setting a flag in the device, or by issuing a communication by the device to a programmer, network, bedside or home monitor, or other target, or by setting an annunciator (a vibrating, audible or visible cue, for example) to alert the patient that a sensing configuration change is needed or has taken place. In addition, the method may actually trigger a change to device function, as noted at 352. Thus, in some examples, a change in sensing configuration may be automatically implemented by the device acting autonomously; in other examples, some intervention or confirmation may be called for before a change is implemented.

Figure 9:
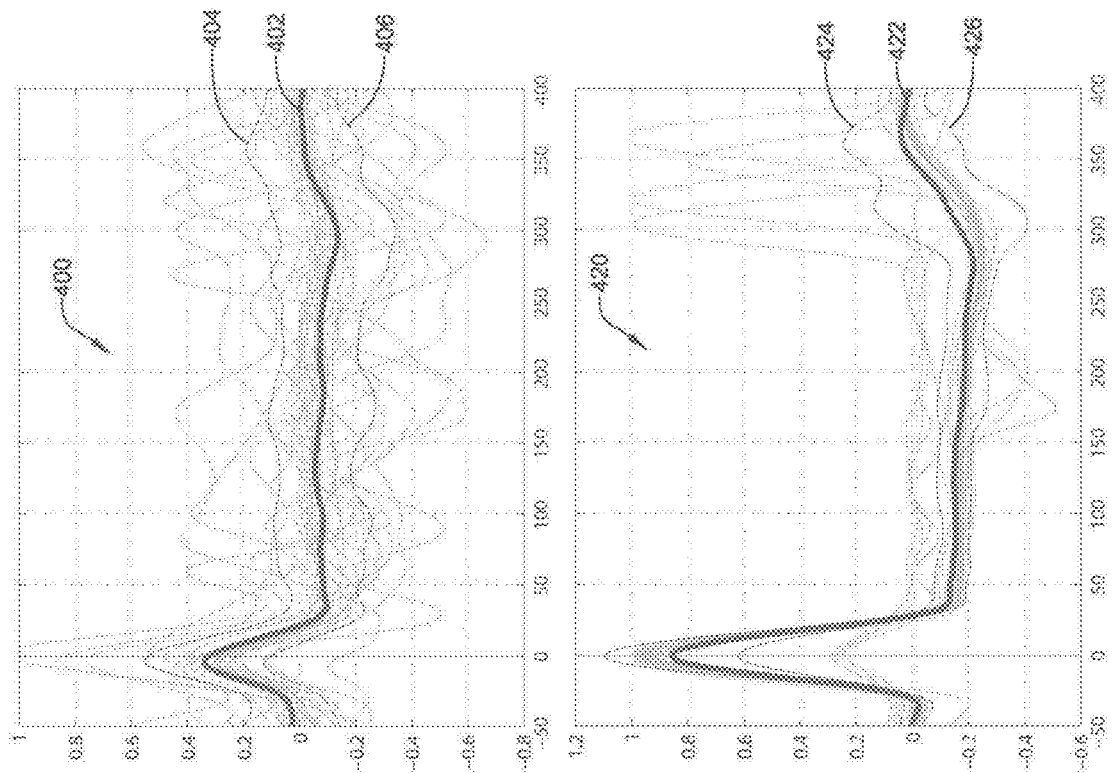
FIG. 9 shows a composite cardiac cycle.

Signal quality metrics can be obtained at each cardiac cycle, then a trend data point may be calculated after n cardiac cycles, as described above and illustrated in FIG. 8. An alternative method is illustrated in FIG. 9, where the signal quality metrics are calculated across a composite cardiac cycle. FIG. 9 shows a composite cardiac cycle as captured across first and second sensing vectors. The composite cardiac cycle provides an analytical tool for assessing sensing vector signal quality by accumulating data for a number of cardiac cycles and generating a comparison of the data across such cycles. The composite cardiac cycle is made up of the data captured in a window defined relative to a plurality of cardiac cycle detections. Several analyses may be performed on the composite cardiac cycle. The horizontal axis may represent a sample number or a point in time for example given in milliseconds, and the vertical axis may represent an actual amplitude in millivolts, for example, or a normalized dimensionless value relative to the sensed range of values or the available dynamic range of the sensing circuitry.

As shown at 400, a number of lines represent the individual signals captured by a device for each of a number of detected cardiac cycles. In the horizontal axis, 0 represents a fiducial point of the plural cycle data. The "0" may be the point in time where each cardiac cycle is detected using a detection threshold approach to detecting cardiac cycles as shown, for example, in U.S. Pat. Nos. 8,565,878 and 5,709,215. Alternatively, the "0" may be a point in time at which the largest amplitude signal for data from each cardiac cycle occurs or another morphologically-based fiducial point in each signal, near detection time, such as the onset of the QRS complex.

Going across the window of data, an "average" signal generated by averaging all the data for each sample point is shown at 402, surrounded by lines 404 and 406 that may represent, for example, plus and minus one standard deviation, or plus and minus the variance, or other statistical metric. Line 402 may be, for example, the mean value or median value at each sample or point in time. In one example, line 404 represents the average at a given point in time of all signals that lie above line 402, while line 406 represents the average at a given point in time of all signals that lie below line 402.

Signal quality metrics may take many forms using the composite cardiac cycle, including, for example, the following:

The amplitude of the peak at or near point "0". A large amplitude indicates better signal quality.

The area under the curve of the absolute value of line 402. A larger area under the curve indicates better signal quality.

The ratio of the peak at or near point "0" to the largest magnitude for one of line 402, 404 or 406. A larger ratio may indicate higher signal to noise ratio and better signal quality.

The area between lines 404 and 406. A wider area may indicate poorer signal quality. The area between lines 404 and 406 may, in one example, be normalized and compared to the area under the curve of line 402.

A count of how many of the individual signals cross outside of a boundary set between lines 404 and 406. A greater number may represent more variability and poorer signal quality.

For any of the above, the analysis may be limited to one or more windows of time insofar as early and late signals (before point 50 and after point 300, for example) may not affect the operation of a cardiac cycle detection algorithm as much as signals more in the center of the window 400.

Using such metrics, one can see from FIG. 9 that the composite cardiac cycle shown at 400 may be inferior to the composite cardiac cycle shown at 420 in several respects including, for example, the narrower spread of lines 424 and 426 compared to the spread of lines 404 and 406 and the greater height of the peaks at point 0 for line 422 as compared to line 402. On the other hand, for a given system, it may be that the composite signal shown at 420 would present a potential hazard as the signal may be too large at point 0 and could threaten to saturate the input circuitry.

As shown by the description here and FIG. 9, the composite cardiac cycles 400, 420 may allow an understanding of signal to noise ratio, variability, amplitude, and/or saturation potential for multiple sensing configurations. These and other metrics may be used to assess signal quality using the composite cardiac cycle.

Figure 10:
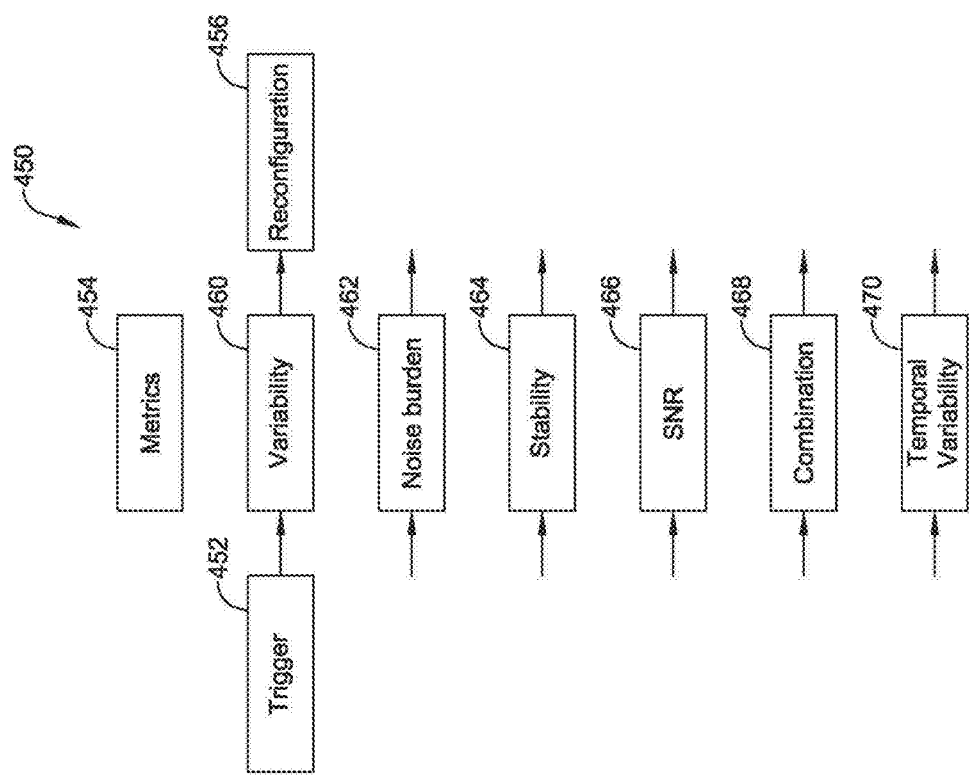
FIGS. 10-13 are block flow diagrams for additional illustrative methods.

FIG. 10 is a block flow diagrams for an illustrative method. The method 450 may start with a triggering condition or event at 452. Triggers are noted above and may include the expiration of a timer or counter, in addition to detected or sensed conditions such as elevated rate, a trend toward poor signal quality, crossing of a signal quality threshold, noise, saturation, overdetection, loss of signal, and other triggers discussed herein. One or plural metrics are then assessed, as indicated at 454. The metrics 454 are used to determine whether to perform sensing reconfiguration at 456 or, alternatively to preserve an existing configuration.

Illustrative metrics in FIG. 10 may include signal amplitude variability 460, which may be calculated across a plurality of detected cardiac cycles. The composite cardiac cycle shown in FIG. 9 may be used. Alternatively, data from individual cycles may be compared against one another using, for example, correlation, difference of area, principal components analysis or other comparative methods. In one example, an autocorrelation as described in U.S. patent application Ser. Nos. 14/819,817, 14/819,851, and 14/819,889 may be performed to determine whether there is high variability. An absence of high correlation scores from the autocorrelation, or other comparative method, may indicate high signal variability for a given sensing vector or configuration, for example.

Other metrics may include the noise burden 462. Noise burden may be calculated in a number of ways including, for example, by determining whether individual detections of cardiac cycles are found to be noisy using beat validation such as in U.S. Pat. No. 7,248,921. Alternatively, noise burden may be identified by assessing the raw signal without relying on whether cardiac cycles are detected, for example by counting turning points or calculating an RMS value of the sensed signal after subtraction of large cardiac signals (QRS complexes, for example, may be windowed out of an RMS calculation). Another illustrative example may use a principal components analysis with one or more components dedicated to representing waves of the cardiac cycle (P, Q, R, S, T, for example); after subtracting out these components from the sensed signal, the remainder can be treated as noise and noise metrics (RMS and maximum peak, for example) can be assessed.

Another metric may be stability, as indicated at 464. Stability can be measured similar to variability, but may also take on a different meaning. For example, sensing stability could be determined by checking on whether the point in time where a new cardiac cycle is detected is stable relative to point in time where the peak amplitude of the cardiac signal for the newly detected cardiac cycle occurs. Stability may also be calculated by observing whether the trend of cardiac signal quality established by some other metric is consistent over time. For example, if the R-wave amplitude is consistent over time for a given sensing vector, that vector may be considered stable, even if other parts of the cardiac cycle vary using a variability metric.

Signal to noise ratio 466 may serve as another metric 454. The SNR can be calculated in several ways identified above. In one example, the peak signal for a cardiac cycle is compared to an average signal for the cardiac cycle or a selected time window of the cardiac cycle to generate an SNR for that particular cycle. In another example, the average peak signal for several cardiac cycles may be compared to an average signal level, or average signal during a selected time window, of the several cardiac cycles.

Another metric may be temporal variability 470. If there is a decrease in signal quality in the presence of noise or oversensing, the temporal variability of detection times peak QRS amplitude, or another fiducial point of the signal will increase.

Finally, combinations 468 of these metrics 454 or other measures may be assessed. The results of the analysis of the metrics 454 can be used to trigger reconfiguration 456. Reconfiguration 456 may rely on the metrics 454, or may refer to other measures of signal quality.

Figure 11:
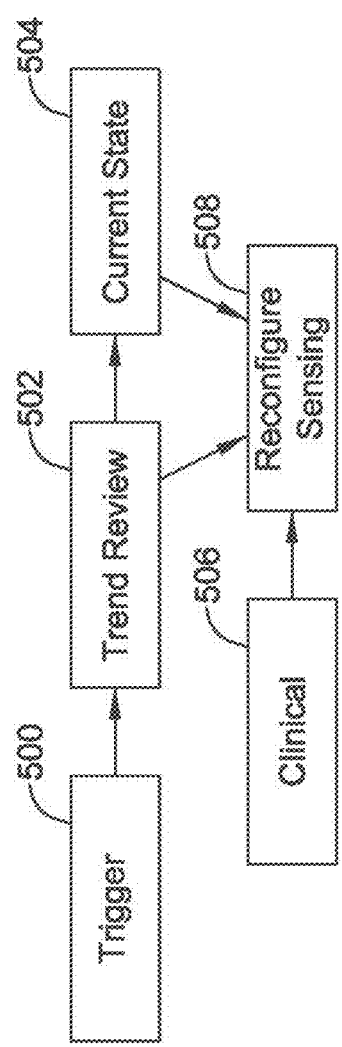

FIG. 11 is a block flow diagram for another illustrative method. Here, following a trigger 500, a trend review 502 is performed by observing cardiac signal quality metrics as calculated over time. The trend review 502 may trigger a review of the current state 504, or review of current state may simply be provided regardless of trend review 502.

Clinical history 506 may also be assessed. This may include review of any relevant clinical event or hazards for one or more sensing configurations. For example, one or more sensing configurations may be eliminated from analysis by virtue of a determination that the sensing configuration has previously been linked to a clinical hazard (inappropriate therapy, for example). In another example, clinical history 506 may determine whether a sensing vector configuration can be eliminated due to fracture, dislodgement or migration of a lead or electrode. In another example, a physician input may be allowed where the physician, at a follow-up, can either indicate that a particular sensing configuration or vector is not to be used, or that a set sensing configuration or vector is not to be changed regardless of any triggering events or trends without physician involvement.

One or several of the trend review 502, current state review 504, and clinical history review 506 can then be used to reconfigure a sensing vector 508.

Figure 12:
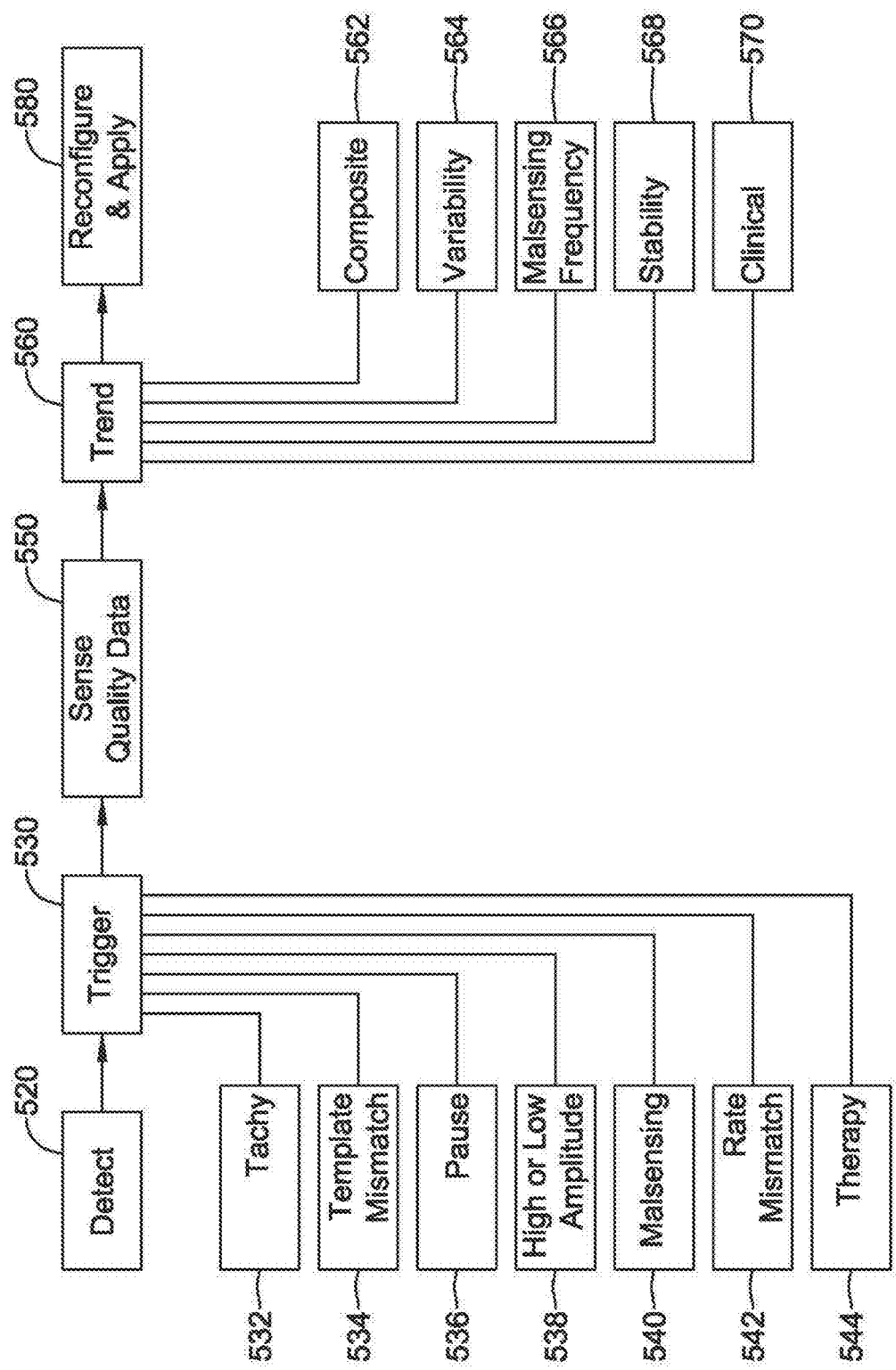

FIG. 12 is a block flow diagram for another illustrative method. The method begins as shown with a detection of a cardiac cycle at 520. This step is optional; the assessment process for signal quality can occur asynchronously relative to the detection of a cardiac cycle 520. For example, asynchronous assessment may use blocks of data in the range of one to ten seconds, or more or less.

Next a trigger event 530. Several trigger conditions are noted. For example, the detection of a tachy condition is shown at 532. Tachy conditions may simply require a cardiac rate exceeding a threshold (which may be fixed or adjustable), or may be more involved as for example calling for a number of intervals to detect (NID) condition to be met or an X-out-of-Y condition to occur. Another trigger may be mismatch to a template at 534. Template mismatch 534 can include persistent failure of detected cardiac cycles to match a static (fixed and stored) or dynamic (continuously changing or changing from time to time as for example where the template is simply a copy of a previously detected cardiac cycle) template. Template mismatch 534 may also occur if a device stores multiple templates and none of the templates are matched, either one time or persistently.

Another trigger may be a long pause between detected cardiac cycles, as noted at 536, which can indicate a loss of signal. The identification of high or low signal amplitude is noted as a trigger at 538. The high amplitude trigger may be found if a signal saturates, or comes near to saturating, an input circuit, or if the signal stays well away from baseline for an extended period of time. A low amplitude trigger may be found if the detected signal fails to exceed a threshold, either across a period of time or as an average or mean. The amplitude triggers 538 may also include the identification of a significant change in average or peak amplitudes.

Malsensing 540 may also be a trigger. Malsensing can include, for example, the identification of overdetected events or detection of noise. Rate mismatch 542 can also be a trigger, where a mismatch can be found if a cardiac cycle rate calculated by a given sensing configuration or vector does not match a rate as calculated using a different sensing vector, or a rate as calculated by a different method (autocorrelation instead of cardiac cycle detection), or using different data (using heart sounds, blood pressure changes or pulse oximetry, for example), or by a different and potentially separate device communicating a detected rate.

Another potential trigger can be the occurrence of therapy delivery 544. In one example, the delivery of any therapy can be a trigger for assessment of cardiac signal quality. In another example, delivery of repeated therapy, indicating at least one therapy attempt did not change a cardiac state (for example, a failed defibrillation shock), may serve as a trigger. Block 544 may be included to account for the potential for inappropriate therapy, for example.

If a trigger 530 occurs, the method can then perform a sense quality data capture step, as noted at 550. In some examples, sensing quality data may be continuously stored or looped to allow immediate and retrospective analysis to take place once a trigger occurs. In other examples, data gathering may occur in response to the trigger 530.

The sense quality analysis in this example may particularly focus on trend data 560. Items like a composite cardiac cycle 562 (FIG. 9), variability 564, frequency of malsensing 566, stability 568, and any relevant clinical history 570 may be included in the trending data.

The analysis in FIG. 12 does not reference assessment of a current condition in block 560, but as noted above in FIG. 11 current status such as the detected amplitude or signal to noise ratio at the time of sensing vector or configuration assessment may also be incorporated. Finally, as shown at 580, sensing may be reconfigured if deemed necessary and a new sensing configuration implemented by the device to begin capturing and analyzing cardiac signal data.

Figure 13:
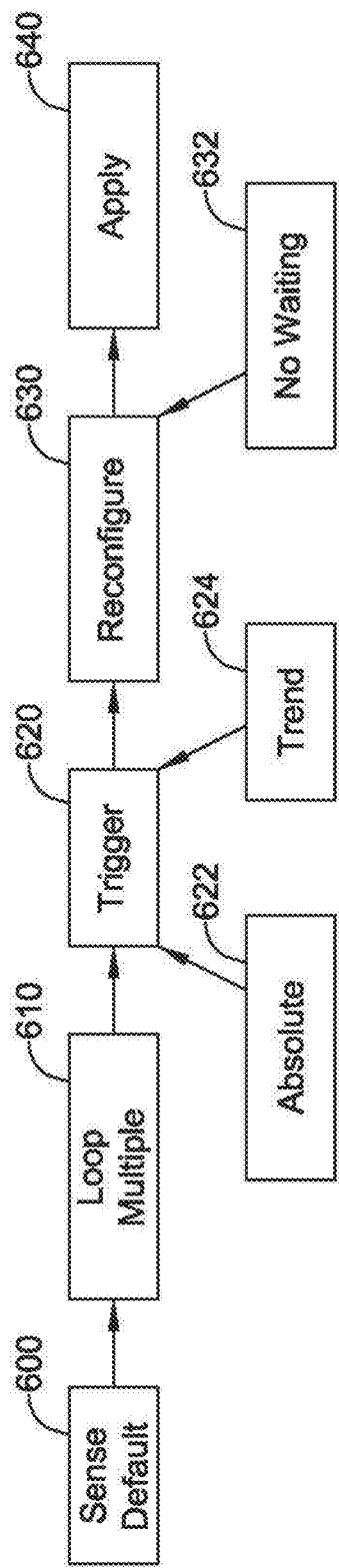

FIG. 13 shows another illustrative method in block flow form. Here, sensing is performed on a default sensing vector, as shown at 600. Meanwhile, data is looped across several sensing vectors as indicated at 610. Looping may include retention of data in a first-in, first-out manner. A trigger 620 is sought using one or more of absolute measures of signal quality 622 and trends of such measures 624. Next, the device or method performs reconfiguration of sensing, as indicated at 630. In some examples, the reconfiguration 630 relies on the stored looped data 610, such that no waiting 632 is required before a new sensing configuration can be applied at 640.

Figure 14:
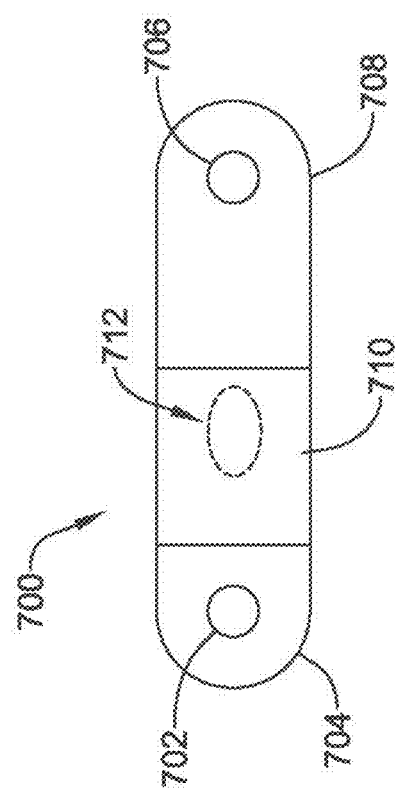
FIG. 14 shows an implantable monitor.

FIG. 14 shows an implantable monitor. An implantable monitor may be implanted subcutaneously in most instances, though other positions such as intracardiac, epicardial, sub-muscular, or below the ribs or behind/beneath the sternum may be used instead. The monitor 700 is shown as having a first sensing electrode 702 on a header 704 that may also include, for example, an antenna for communicating with an external or second internal device. A second sensing electrode is shown at 706 on the opposite end of the device 700 from the first electrode 702. The second sensing electrode may be provided on the outside of a battery 708, for example, which may or may not be rechargeable. Operational circuitry for this design may be provided in the central portion of the device, as indicated at 710. A third sensing electrode 712 is shown in phantom to indicate that it may be on the opposite side of the device from the first and second electrodes 702, 706. Other dispositions of the multiple electrodes may be used instead, such as those shown in U.S. Pat. No. 5,331,966, or those used in commercially available implantable cardiac monitors such as the various Medtronic Reveal™ products.

Figure 15:
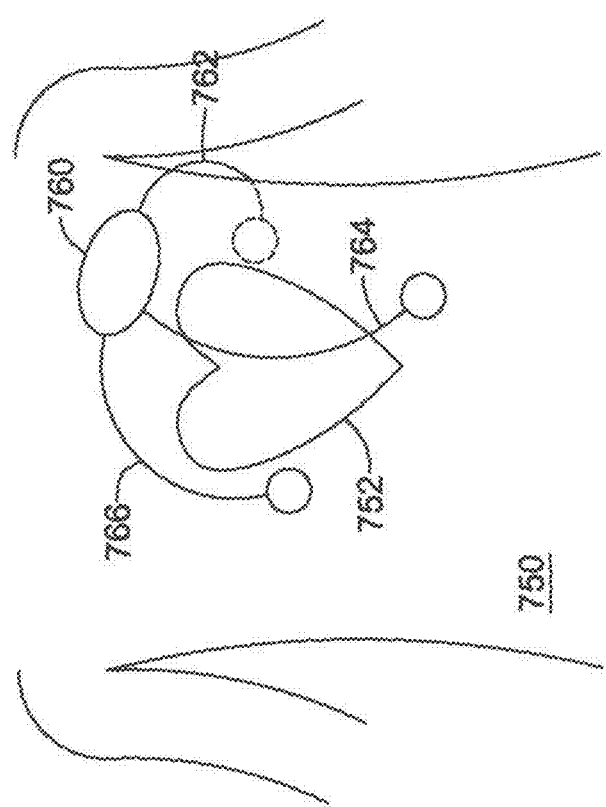
FIG. 15 illustrates a wearable cardiac rhythm management device.

FIG. 15 illustrates a wearable cardiac rhythm management device. The system is shown on the torso 750 of a patient relative to the heart 752 of the patient. The external device may include, for example, a canister 760 having a power source and operational circuitry for the device, as well as a plurality of leads 762, 764, 766 connected to cutaneous electrodes on the front or back of the patient's torso 750. It is understood that the system may provide therapy or may be merely a monitor, and may take other forms. The system may be, for example, integrated in a wearable vest, or provided as an automated external defibrillator, or may be a smaller wearable product such as a Holter monitor or wearable patch, for example.

For the purposes of the present invention, the implantable therapy system (FIG. 1), implantable monitor (FIG. 14), or external device for therapy or monitoring (FIG. 15) may integrate the various improvements shown herein so long as there are multiple sensing configurations available. While most of the above discussion focuses on the availability of multiple sensing vectors, a sensing reconfiguration may instead call for changing one or more of sensing gain, sensing filtering, data rate, sampling rate, or other sensing features, in addition to or instead of simply considering a different sensing vector.

Various examples above may be implemented in wearable or implantable devices such as the devices shown in FIGS. 1, 14 and 15. Such implementation may take place by including operational circuitry for receiving a signal from implantable electrodes, processing the signal and analyzing the processed signal to make decisions such as whether to store data or deliver therapy. Operational circuitry may be housed in a canister or canisters. The operational circuitry may include a controller (such as a microcontroller or microprocessor, or simply an application specific integrated chip (ASIC) such as an analog, mixed signal, or digital ASIC). The operational circuitry may instead or also include suitable analog and/or digital circuits needed for signal processing, memory storage and generation of high-power electrical, low-power electrical and/or non-electrical outputs. The operational circuitry may include suitable battery technology for an implantable device (rechargeable or primary cell), with any of numerous examples well known in the art, and may use various capacitor technologies to assist in the short term build-up and/or storage of energy for defibrillation or other output purposes. The implantable or wearable components may be manufactured with biocompatible materials suitable for implantation or tissue contact, such as those widely known, along with coatings for such materials, throughout the art. For example, implantable devices can be made using titanium, with a titanium nitride or iridium oxide (or other material) coating if desired, and implantable leads can be formed with a biocompatible material such as a polyether, polyester, polyamide, polyurethane, polycarbonate, silicon rubber and blends or copolymers thereof. Alternatively, other biocompatible materials such as silver, gold, titanium, or stainless steel such as MP35N stainless steel alloy, or other materials may be used.

In some examples, the system may include one or more sensors to detect signals in addition to the cardiac electrical signal that can be captured using selected combinations of implantable or wearable electrodes. Such additional sensors may include, for example, temperature sensors, accelerometers, microphones, optical sensors and chemical sensors, among others. The programmer 22 and implantable device 12 may communicate with one another using, for example and without limitation, inductive or RF telemetry, or any other suitable communication solution. The present invention may be embodied in a system having any such characteristics.

A first non-limiting example takes the form of a cardiac rhythm management device for use with a patient having a plurality of electrodes coupled to sensing circuitry to allow a plurality of sensing configurations to be defined thereby and operational circuitry (such as devices and systems shown in FIGS. 1, 14, and 15) comprising the following: detector means for detecting cardiac cycles of the patient using a first sensing configuration (such as circuitry and or programming instructions represented in FIG. 2, block 80, or FIG. 12, block 520, for example); trigger means for identifying a triggering event for sensing reconfiguration analysis (such as circuitry and or programming instructions represented in FIG. 7, block 280, FIG. 8, block 340, FIG. 10, block 452, FIG. 11, block 500, FIG. 12, block 530, and/or FIG. 13, block 620, for example); analyzer means for analyzing sensing quality data comprising data from two or more cardiac cycles of the patient for one or more sensing vectors, in which a sensing vector is defined between at least two of the plurality of electrodes (such as circuitry and or programming instructions represented in FIG. 8, block 344, and/or FIG. 12, block 550, for example); identifier means for identifying a trend indicating one or more unfavorable sensing configurations (such as circuitry and or programming instructions represented in FIG. 11, block 502 and/or FIG. 12, block 560, for example); selector means for selecting a sensing reconfiguration which is not one which has been identified as unfavorable in light of the trend (such as circuitry and or programming instructions represented in FIG. 10, block 456, FIG. 11, block 508, FIG. 12, block 580, and/or FIG. 13, block 630, for example); and a means for applying the sensing reconfiguration to detect and analyze cardiac signal data (such as circuitry and or programming instructions represented in FIG. 8, block 352, FIG. 12, block 580 and/or FIG. 13, block 640, for example).

A second non-limiting example takes the form of a cardiac rhythm management device as in the first non-limiting example, the identifier means is configured for capturing data within sensing windows defined for several of the detected cardiac cycles (FIG. 9, for example); calculating a composite variability factor by analysis of the data captured within each sensing window (such as circuitry and or programming instructions represented in FIG. 12, block 562, for example); and finding that the variability factor indicates relatively high variability for one or more sensing configurations.

A third non-limiting example takes the form of a cardiac rhythm management device as in the second non-limiting example, wherein each sensing window comprises a plurality of sample points and the variability factor is determined by calculating one or more of a variance; a standard deviation, or a range of detected signal amplitudes on a sample by sample basis within the sensing windows (such as circuitry and or programming instructions represented in FIG. 12, block 562 or FIG. 9, for example).

A fourth non-limiting example takes the form of a cardiac rhythm management device as in the first non-limiting example, wherein the identifier means is configured for: receiving indications of new cardiac cycles from detector means for detecting a plurality of cardiac cycles of the patient (detector means may comprise circuitry and or programming instructions represented by blocks 80 in FIG. 2 and/or block 520 in FIG. 12); calculating a signal quality metric for each cardiac cycle; observing variability of the signal quality metric for the plurality of cardiac cycles; and finding high variability of the signal quality metric (such as circuitry and or programming instructions represented in FIG. 12, block 562 or FIG. 9, for example).

A fifth non-limiting example takes the form of a cardiac rhythm management device as in the first non-limiting example, wherein the identifier means is configured for receiving indications of a plurality of cardiac cycle detections from detection means analyzing the plurality of cardiac cycles to identify one or more of noise or overdetection; calculating a frequency with which one or more of noise or overdetection occurs; and finding a high frequency of occurrence of noise or overdetection (such as circuitry and or programming instructions represented in FIG. 8, block 308 or FIG. 12, block 566, for example).

A sixth non-limiting example takes the form of a cardiac rhythm management device as in the first non-limiting example, wherein the identifier means is configured for receiving indications from cardiac cycle detection means that a plurality of cardiac cycles of the patient have been detected; analyzing the plurality of cardiac cycles to identify one or more of noise or overdetection; determining how often one or more of noise or overdetection occurs as a function of time; and finding that the frequency of occurrence of noise or overdetection is increasing with time (such as circuitry and or programming instructions represented in FIG. 12, block 566, for example).

A seventh non-limiting example takes the form of a cardiac rhythm management device as in the first non-limiting example, wherein the identifier means is configured for receiving indications from detector means for detecting a plurality of cardiac cycles of the patient with each of first and second sensing configurations; calculating stability of a signal quality metric for each of the first and second sensing configurations over time including a plurality of detected cycles; and identifying whichever of the first and second sensing configurations has less stability of the signal quality metric (such as circuitry and or programming instructions represented in FIG. 12, block 568, for example).

An eighth non-limiting example takes the form of a cardiac rhythm management device as in any of the first seven non-limiting examples wherein the trigger means is configured to identify a trigger event when one of the following occurs: an X-out-of-Y threshold or number of intervals to detect threshold met, indicating that a potential tachyarrhythmia may be occurring (such as circuitry and or programming instructions represented in FIG. 12, block 532, for example); a calculated cardiac rate rises above threshold (such as circuitry and or programming instructions represented in FIG. 12, block 542, for example); failure of a stored template to match a data from a plurality of detected cardiac cycles (such as circuitry and or programming instructions represented in FIG. 12, block 534, for example); a long pause between detected cardiac cycles (such as circuitry and or programming instructions represented in FIG. 12, block 536, for example); a low amplitude event is identified in which the cardiac signal amplitude fails to reach a defined low amplitude threshold in a defined manner (such as circuitry and or programming instructions represented in FIG. 12, block 538, for example); a saturation event is identified in which the cardiac signal amplitude exceeds a defined high amplitude threshold in a defined manner (such as circuitry and or programming instructions represented in FIG. 12, block 538, for example); identification of a plurality of cardiac cycles as one of noise or overdetected (such as circuitry and or programming instructions represented in FIG. 12, block 540, for example); cardiac rate determined using the detected cardiac cycles fails to match a cardiac rate calculated by a different operation selected from the group consisting of autocorrelation, heart sounds, data from a second device, blood pressure monitoring, and pulse oximetry (such as circuitry and or programming instructions represented in FIG. 12, block 542, for example); and delivery of an electrical cardiac therapy to the patient (such as circuitry and or programming instructions represented in FIG. 12, block 544, for example).

A ninth non-limiting example takes the form of a cardiac rhythm management device having a plurality of sensing electrodes defining at least first and second sensing vectors coupled to operational circuitry configured to select a default sensing vector from among the at least first and second sensing vectors (for example, a device as in any of FIGS. 1, 14 and 15), wherein the operational circuitry comprising the following: analyzer means for analyzing a cardiac signal captured using the default sensing vector to determine whether an arrhythmia appears to be present with one or more sensing vectors that are not the default sensing vector disabled (such as circuitry and or programming instructions represented in FIG. 13, block 600, for example); a first means for determining that an arrhythmia is likely occurring (such as circuitry and or programming instructions represented in FIG. 13, block 620, for example); a second means for enabling one or more of the disabled sensing vectors to capture data (such as circuitry and or programming instructions represented in FIG. 13, block 630, for example); and a third means for storing data captured from each of the default sensing vector and the one or more enabled sensing vectors for use in later diagnostic work (such as circuitry and or programming instructions represented in FIG. 13, block 640, for example).

A tenth non-limiting example takes the form of a cardiac rhythm management device having a plurality of sensing electrodes defining at least first and second sensing vectors coupled to operational circuitry configured to select a default sensing vector from among the at least first and second sensing vectors (such as a device as in any of FIGS. 1, 14 and 15), wherein the operational circuitry comprising the following: a first means for storing at least temporarily an output on each of the first and second vectors (such as circuitry and/or programming instructions represented at block 610 of FIG. 13 for looping recording of data, an identifier means for identifying a triggering condition for reconfiguration of sensing (such as circuitry and/or programming instructions represented at block 620 of FIG. 13) using whichever of the first and second vectors is identified as primary; and an analyzer means for analyzing the data stored at least temporarily for each of the first and second vectors to determine which of the first and second vectors provides better quality sensing (such as circuitry and/or programming instructions represented at block 630 of FIG. 13); wherein the operational circuitry is configured to analyze the data without waiting for additional data to be received after the triggering condition is identified (as pointed out at block 632 of FIG. 13, and facilitated by circuitry and/or programming instructions represented again at block 630 of FIG. 13).

An eleventh non-limiting example takes the form of a cardiac rhythm management device having a plurality of sensing electrodes defining at least first and second sensing vectors coupled to operational circuitry configured to select a default sensing vector from among the at least first and second sensing vectors comprising the following: identifier means for identifying a current state of one or more signal quality metric for at least each of the first and second sensing vectors (such as circuitry and or programming instructions represented in FIG. 4, block 170, for example); a first analyzer means for analyzing historical data for each of the first and second sensing vectors to identify a long term trend of one or more signal quality trend metrics (such as circuitry and or programming instructions represented in FIG. 4, block 180, for example); a second analyzer means for analyzing analyze historical data for at least one of the first and second sensing vectors to identify any clinical hazards (such as circuitry and or programming instructions represented in FIG. 4, block 180, for example); and means for combining the current state, long term trend, and clinical hazards to select the default sensing vector (such as circuitry and or programming instructions represented in FIG. 4, block 170, for example).

A twelfth non-limiting example takes the form of a cardiac rhythm management device as in any of the first eleven non-limiting examples wherein the device is a wearable cardiac rhythm management device adapted to deliver therapy (such as shown in FIG. 15).

A thirteenth non-limiting example takes the form of a cardiac rhythm management device as in any of the first eleven non-limiting examples wherein the device is a wearable cardiac monitoring device (such as shown at FIG. 15).

A fourteenth non-limiting example takes the form of a cardiac rhythm management device as in any of the first eleven non-limiting examples wherein the device is an implantable cardiac rhythm management device adapted to deliver therapy (such as shown in FIG. 1).

A fifteenth non-limiting example takes the form of a cardiac rhythm management device as in any of the first eleven non-limiting examples wherein the device is an implantable cardiac monitoring device (such as shown in FIG. 14).

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
a cardiac rhythm management device having a plurality of sensing electrodes defining at least first and second sensing vectors coupled to operational circuitry configured to select a default sensing vector from among the at least first and second sensing vectors, wherein the operational circuitry is configured to perform the following:
analyzing a cardiac signal captured using the default sensing vector to determine whether an arrhythmia appears to be present, while a set of disabled sensing vectors that does not include the default sensing vector is disabled;
determining that an arrhythmia is likely occurring using analysis of the cardiac signal captured using the default sensing vector;
responsive to determining that an arrhythmia is likely occurring, enabling one or more disabled sensing vectors from the set of the disabled sensing vectors to capture data; and
storing data captured from each of the default sensing vector and the one or more enabled sensing vectors while the arrhythmia is likely occurring; and
a programmer for use by a user to set parameters of the cardiac rhythm management device, wherein the programmer is configured to present the stored data from the one or more enabled sensing vectors to the user
wherein at least one of the programmer or the cardiac rhythm management device is configured to generate a report, and the report includes a simulation of how at least one of the one or more enabled sensing vectors would have been analyzed.

2. The system of claim 1, wherein the operational circuitry is configured to deliver therapy in response to the detected arrhythmia, and, after delivering the therapy, to analyze the stored data to determine whether to switch default sensing vectors to one of the disabled sensing vectors.

3. The system of claim 1 wherein the report comprises at least part of the stored data for display to the user of the programmer.

4. The system of claim 3 wherein the report includes a visual image of a signal from at least one of the one or more enabled sensing vectors.

5. The system of claim 1 wherein the simulation is performed in accordance with programmed settings of the cardiac rhythm management device.

6. The system of claim 1 wherein the programmed settings include a rate boundary for defining whether the arrhythmia is treatable.

7. The system of claim 1 wherein the operational circuitry is further configured to determine a quality of the default sensing vector using at least part of the stored data.

8. A method of using a cardiac rhythm management device having a plurality of sensing electrodes defining at least first and second sensing vectors coupled to operational circuitry configured to select a default sensing vector from among the at least first and second sensing vectors, the method comprising:
analyzing a cardiac signal captured using the default sensing vector to determine whether an arrhythmia appears to be present with a set of disabled sensing vectors that does not include the default sensing vector disabled;
determining that an arrhythmia is likely occurring;
responsive to determining that the arrhythmia is likely occurring, enabling one or more disabled sensing vectors from the set of the disabled sensing vectors to capture data;
storing data captured while the arrhythmia is likely occurring from each of the default sensing vector and the one or more enabled sensing vectors; and
presenting at least part of the stored data in a report that also includes a simulation of how at least one of the one or more enabled sensing vectors would have been analyzed.

9. The method of claim 8 wherein the report includes a visual image of a signal from at least one of the one or more enabled sensing vectors.

10. The method of claim 8 wherein the simulation is performed in accordance with programmed settings of the cardiac rhythm management device.

11. The method of claim 10 wherein the programmed settings include a rate boundary for defining whether the arrhythmia is treatable.

12. The method of claim 8 further comprising:
determining a quality of the default sensing vector using at least part of the stored data.

13. The method of claim 12 wherein the quality of the default sensing vector is determined after the arrhythmia has ended.

\* \* \* \* \*